United States Patent [19]

Bonnefous

[11] Patent Number: 5,062,430

[45] Date of Patent: Nov. 5, 1991

[54] DEVICE FOR MEASURING THE SPEED OF BLOOD FLOWS BY ULTRASONIC ECHOGRAPHY AT AN INCREASED MEASURING SPEED

[75] Inventor: Odile Bonnefous, Nogent sur Marne, France

[73] Assignee: U.S. Philips Corporation, New York, N.Y.

[21] Appl. No.: 518,896

[22] Filed: May 4, 1990

[30] Foreign Application Priority Data

May 12, 1989 [FR] France ............................ 89 06289

[51] Int. Cl.⁵ .............................................. A61B 8/06
[52] U.S. Cl. .............................. 128/661.09; 73/861.25
[58] Field of Search ................... 128/661.07, 661.08, 128/661.09, 661.10; 73/861.25

[56] References Cited

U.S. PATENT DOCUMENTS

| 4,761,752 | 8/1988 | Barnes | 364/728 |
| 4,803,990 | 2/1989 | Bonnefous et al. | 128/661.08 |
| 4,809,249 | 2/1989 | Barnes | 128/661.08 |
| 4,825,422 | 4/1989 | Takeda | 128/661.08 |
| 4,853,904 | 8/1989 | Pesque | 128/661.08 |
| 4,883,060 | 11/1989 | Pesque et al. | 128/661.09 |
| 4,928,698 | 5/1990 | Bonnefous | 128/661.09 |

Primary Examiner—Francis Jaworski
Assistant Examiner—George Manuel
Attorney, Agent, or Firm—William Squire

[57] ABSTRACT

A device for the measurement of the speed of blood flows on the basis of a sequence of N successive echographic signals, comprising an M-point fixed-echo elimination device (200), followed by a unit (300) for measuring the speed by correlation/summation/interpolation of the $N-M+1$ independent signals supplied by the fixed-echo elimination device (220). In accordance with the invention, the measuring unit (300) comprises $N_F$ parallel processing channels (310j), each of which is formed by a filter (311j), a memory (312j) for storing the filtered $N-M+1$ signals, and a correlation device (313j) which supplies $N-M$ intercorrelation functions, and on the other hand an adder (320) which forms the mean value of the $N_F(N-M)$ intercorrelation functions obtained, an estimate of the relevant speed being supplied by an interpolation circuit (330) acts on the mean intercorrelation function.

8 Claims, 2 Drawing Sheets

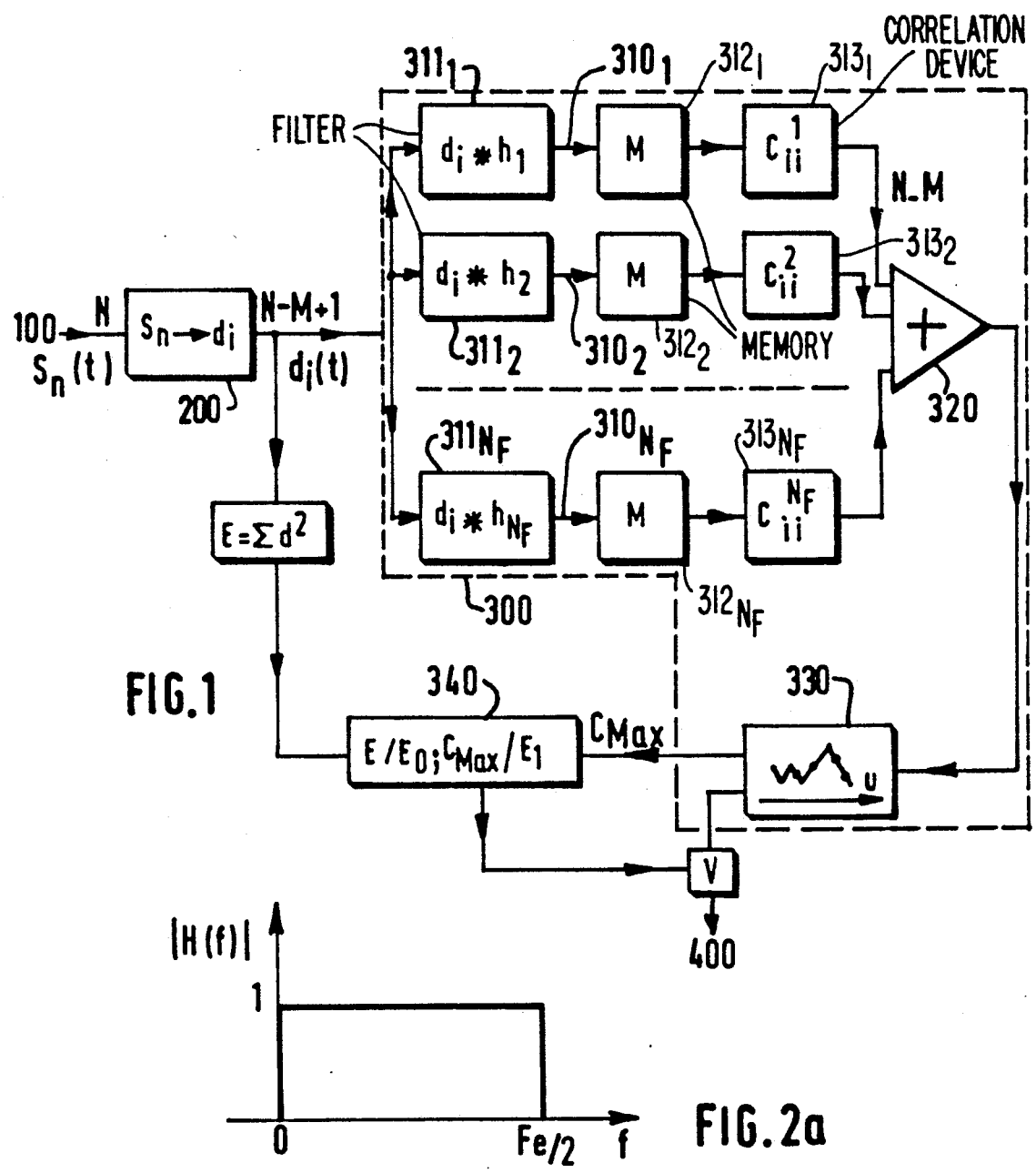
FIG.1
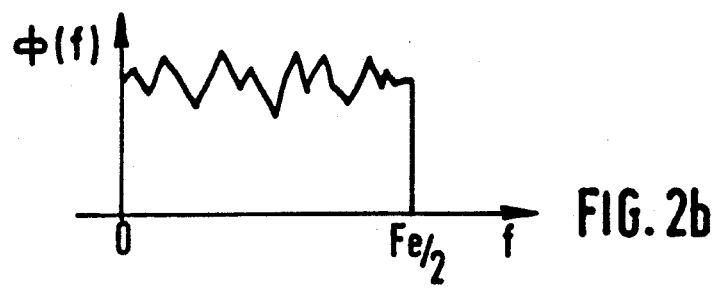
FIG.2a
FIG.2b

DEVICE FOR MEASURING THE SPEED OF BLOOD FLOWS BY ULTRASONIC ECHOGRAPHY AT AN INCREASED MEASURING SPEED

The present invention relates to a device for measuring of the speed of blood flows on the basis of a sequence of N successive echographic signals, comprising an M-point fixed-echo elimination device, followed by a unit for measuring the speed by correlation/summation-/interpolation of the $N-M+1$ independent signals supplied by the fixed-echo elimination device.

The invention is used particularly advantageously in the general field of echographic examination of blood flows in vessels, notably for the imaging of such flows.

From European Patent Application No. 0 225 667 corresponding to U.S. Pat. No. 4,803,990 there is known a measuring device of the kind set forth in which the measuring unit is formed by a memory in which the $N-M+1$ independent signals are stored, a correlation device which supplies $M-N$ intercorrelation functions for the $M-N+1$ signals stored, an adder which supplies the mean intercorrelation function, and an interpolation circuit which enables determination of the maximum of the mean intercorrelation function, also referred to as the correlation peak, whose position is linked directly to the relevant speed of the flows. Actually, it can be recalled that the known device utilizes the fact that the successive ultrasonic signals returned by a moving target are linked by the following equation:

$$S_{n+1}(t) = S_n(t-\tau)$$

in the case of a recurrent transmission with a recurrent period T. This signifies that the signal $n+1$ is the replica of the preceding signal n, except for a time shift $\tau$. The latter represents the supplementary time required by the ultrasonic wave in order to travel the path from the transducer to the target and back to the transducer from one excitation to another. In other words:

$$\tau = 2\, VT/C$$

where V is the speed of the target and C is the speed of sound. It appears that measurement of $\tau$ enables measurement of the relevant speed V.

The intercorrelation function between $S_n(t)$ and $S_{n+1}(t)$ which, in a window having the width W, is defined by the relation:

$$C_{n,\,n+1}(tO, u) = \int_{tO}^{tO+W} S_{n+1}(t+u)S_n(t)dt$$

verifies:

$$C_{n,\,n+1}(tO, u) = C_{nn}(tO, u-\tau)$$

The time tO is linked to the scanning depth z as $tO = 2z/C$.

The function $C_{nn}(tO, u)$ is an autocorrelation function and is, therefore, maximum for $u=0$.

Thus, a measure of the time shift $\tau$ and hence of the speed V, can be obtained by searching for which parameter u the function $C_{n,\,n+1}(tO, u)$ is maximum. If this maximum is obtained for the value uO of u, $\tau$ is deduced therefrom by utilizing the equality $uO =$ and $V = uOC/2T$.

The device described in the cited European Patent Application has made a decisive contribution to the measurement of the speed of blood flows and to their imaging. It is to be noted, however, that the precision of the result obtained depends on the number of intercorrelation functions for which the mean value is formed, that is to say $N-M$ for the known device. In order to reduce the variance of the measurement it is, therefore, advantageous to increase the number N of signals to be simultaneously processed, or to decrease the number of points M of the fixed-echo elimination device. In practice it is hardly possible to reduce M to substantially less than 3 or 4. It is known that the use of a fixed-echo elimination device is indispensable, before any estimation of the speed profile, because of the high reflectivity of the walls of the vessels which may exceed the reflectivity of blood (white cells) by 40 dB. The simplest fixed-echo elimination device is that which is referred to as a 2-point device which consists of a delay line equaling one recurrent period in parallel with a zero delay line. Weighting coefficients of $+1$ and $-1$, respectively, are attached to these lines which, after weighting, are added by an adder. This known filter thus forms the difference between two consecutive echographic lines which, in principle, leads to a quasi-complete reduction of the echos produced by the fixed tissues. However, this technique has a major drawback in that it also attenuates the signals corresponding to low flow speeds. For example, it can be demonstrated that the response of the above filter as a function of the flow speed is such that for a recurrent frequency of 5 kHz and a transmission frequency of 5 MHz, a signal corresponding to $v=5$ cm/s is attenuated by 30 dB. This makes it difficult or impossible to measure the flow speeds where they are lowest, that is to say near the walls of the vessels. However, knowledge of these speeds is very important for the study and the clinical diagnosis of arteries, for example. Therefore, use is preferably made of an echo elimination device comprising at least 3 points as described in European Patent Application No. 0 298 569 corresponding to U.S. Pat. No. 4,883,060, which enables complete elimination of the echos produced by the fixed tissues, however, without excessively reducing the signals originating from low-speed flows.

It can be concluded that the only way to improve the measurement precision will be to increase the number N of successive signals used for obtaining an estimate of the speed. However, it will be clear that this solution has the direct consequence that it decreases the measuring speed, or the imaging speed in the case of display, which is given by 1/NT.

The technical problem to be solved by the present invention is to realize a measuring device of the kind set forth which enables a higher measuring precision to be achieved without affecting the speed or enables, which is the same, the measuring speed to be increased without reducing the precision.

The solution to the technical problem posed in accordance with the invention consists in that the measuring unit comprises on the one hand $N_F$ parallel processing channels, each of which is formed by a filter, a memory for storing the $N-M+1$ filtered signals, and a correlation device which supplies $N-M$ intercorrelation functions, and on the other hand an adder which forms the mean value of the $N_F(N-M)$ intercorrelation functions obtained, an estimate of the relevant speed being supplied by an interpolation circuit which acts on the mean intercorrelation function. The essential technical effect on which the invention is based thus resides in the multiplication, by a factor $N_F$, of the number of independent intercorrelation functions on the basis of which the mean intercorrelation function is calculated. This is made possible by the fact that the filtering operations preserve the time relations between the signals and, consequently, lead to the same correlation results. The independence of the intercorrelation functions obtained by the various parallel processing channels is ensured by the absence of correlation between the $N_F$ filters. Thus, for the same measuring frequency $1/NT$ there is obtained a speed estimate whose precision has been improved by a factor $\sqrt{N_F}$. Conversely, if $1/NOT$ is the measuring speed of the known device described above which produces the same precision as the device in accordance with the invention, the relation between N and NO is given by:

$$N_F(N-M) = NOM$$

so $$N = (NO-M)/N_F + M$$

where NO = 15, M = 3 and $N_F = 6$, so N = 5, this corresponds to a gain of a factor 3 as regards the measuring speed. It is to be noted, however, that when the number $N_F$ of parallel processing channels is increased, a limit value arises for N equal to M.

The choice of the $N_F$ filters is based on the idea to realize artifically $N_F$ different piezoelectric transducers by applying different filtering operations to a single transducer, without risking the degradation of the signal resolution. Therefore, in a specific embodiment in accordance with the invention where Fe is the sampling frequency of the device, each filter is defined on the interval ]O, Fe/2] by a modulus response equal to 1 and a random phase, and by a response zero for the frequency zero. Each of the $N_F$ filters is thus characterized by its random phase distribution. It is also to be noted that this type of filter preserves the frequency band of the signals.

Finally, in known manner use can be made of a method of utilizing the correlation which is referred to as a "1-bit" correlation and in which each memory stores only the sign of the $N-M+1$ signals supplied by the corresponding filter. In this case the peak of the intercorrelation function is shaped as an isosceles triangle. Knowledge of this shape enables a complete reconstruction, starting from the highest point and its two neighbors, of the correlation peak by linear interpolation and hence enables precise determination of the position uO of its maximum.

The invention will be described in detail hereinafter, by way of example, with reference to the accompanying diagrammatic drawings. Therein:

FIG. 1 shows a diagram of a measuring device in accordance with an embodiment of the invention.

FIGS. 2a and 2b show the frequency response and the phase of filters used in the device shown in FIG. 1.

Figure 3:
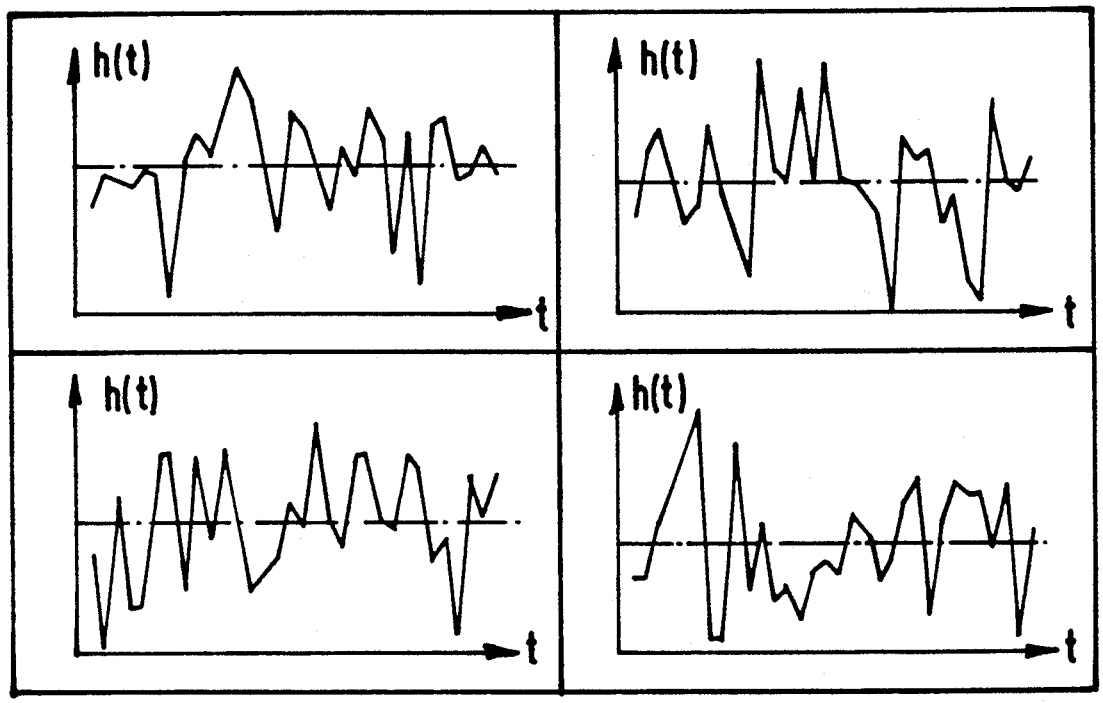
FIG. 3 shows some examples of the time response of filters having a frequency response as shown in FIG. 2.

FIG. 1 diagrammatically shows a device for measuring the speed of blood flows on the basis of a sequence of N successive echographic signals $S_n(t)$, n varying in steps of 1 from 1 to N. These echographic signals originate from a transmitter/receiver unit 100 (not shown) which comprises, in a conventional manner, a piezoelectric transducer which converts the electric excitation signals which it receives from a transmitter stage into periodic trains of ultrasonic pulses having a recurrent period T. A receiver stage outputs the echographic signals $S_n(t)$, sampled at the sampling frequency Fe, which signals are returned to the piezoelectric transducer through the medium being studied. The speed measuring device of FIG. 1 comprises an M-point fixed-echo elimination device 200 which produces, from the sequence of N echographic signals $S_n(t)$, a sequence of $N-M+1$ independent signals $d_i(t)$ which do not contain high amplitude components originating from fixed walls of the vessels. As has been indicated above, an example of a fixed-echo elimination device which comprises M = 3 points and which would be suitable for the device in accordance with the invention is described in European Patent Application No. 0 298 569.

As appears from FIG. 1, the fixed-echo elimination device 200 is followed by a unit 300 for measuring the speed V of the relevant blood flow by correlation/summation/interpolation of the $N-M+1$ independent signals $d_i(t)$ supplied by the fixed-echo elimination device in conformity with European Patent Application No. 0 225 667. As appears from FIG. 1, the measuring unit 300 comprises first of all $N_F$ parallel processing channels denoted as 310j, where j = 1, 2, ... $N_F$. Each of these processing channels comprises a filter 311j, whose response H(f) as a function of the frequency f is diagrammatically shown in the FIGS. 2a and 2b: the modulus $|H(f)|$ is 0 for f = O and 1 from the frequency 0 to the frequency Fe/2, where Fe is the sampling frequency, the phase $\phi(f)$ being, in the same interval, a random function of the frequency:

$$\phi(f) = Ran(f)$$

Some examples of time responses h(t) of filters of this type are given in FIG. 3. The four filters shown in this Figure have the property that they are fully decorrelated between themselves, ensuring complete independence of the $N_F$ processing channels from one another; this property is essential to ensure the effectiveness of the device in accordance with the invention. The operation performed by the filters 311j is a convolution which produces, for the input signal $d_i(t)$, on the output the signal $d_i^j(t)$ equal to:

$$d_i^j(t) = d_i(t) \times h_j(t).$$

Subsequently, the channel 310j comprises a memory 312j for storing the values of the $N-M+1$ filtered signals $d_i^j(t)$ which serve for the calculation, using a correlation device 313j, of the $N-M$ intercorrelation functions defined by:

$$C_{ii}^j(tO, u-\tau) = C_{i,i+1}^j(tO, u) = \int_{tO}^{tO+W} d_{i+1}^j(t+u)d_i^j(t)dt.$$

The signals $d_i^j(t)$ used for determining the intercorrelation functions can be limited to only the signs of the signals themselves. This method substantially simplifies the correlation calculations and also the size of the memories 312j because the signals processed occupy only a 1-bit word therein.

The filtering by the filters 311j does not affect the correlation result, because the convolution does not modify the time relations between signals; in other words:

$$\int_{tO}^{tO+W} d^j_{i+1}(t+u)d^j_i(t)dt = \int_{tO}^{tO+W} d_{i+1}(t+u)d_i(t)dt,$$

regardless of j.

This property enables $N_F(N-M)$ independent intercorrelation functions to be effectively obtained, the mean value thereof being formed by an adder 320. Due to the impedance of the correlation functions, the mean correlation function:

$$C(tO, u-) = \sum_{i,j} C^j_{ii}(tO, u-\tau)$$

presents a variance $\delta^2$ divided by $N_F$.

Finally, the function $C(tO, u-\tau)$ is processed in a conventional manner by an interpolation device 330 which supplies the estimate V of the relevant speed by calculating the position $uO = \tau = 2VT/C$ of the correlation peak whose height $C_{Max}$ is also measured in order to be used in a circuit 310 for validating the estimated value V of the speed.

The validation of the speed measurement is indispensable. This is because outside the flow zones the output signal of the fixed-echo elimination device 200 is essentially noise. The result thus supplied by the device in accordance with the invention is not an indication of a speed zero, and it is necessary to validate, or not, this result. Therefore, two comparisons are performed. On the one hand, the local energy E of the output signal of the fixed-echo elimination device is calculated:

$$E = \sum_{i=1}^{N-M+1} d_i^2(t)$$

Subsequently, E is compared with a threshold $E_0$. If the result of this comparison is positive, the maximum $C_{Max}$ of the correlation peak is compared with a second threshold $E_1$. The estimate V of the speed will be validated only if $C_{Max}$ is greater than $E_1$.

The speed thus validated is processed for display in a conventional manner by a unit 400 (not shown) which comprises a device for storage, scan conversion and colour encoding.

What is claimed is:

1. A device for measuring the speed of blood flow comprising:
   M-point fixed-echo elimination means responsive to a sequence of N successive echographic signals applied thereto for producing $N-M+1$ independent output signals, where M and N are positive integers;
   $N_F$ parallel processing channels each comprising filter means for filtering said $N-M+1$ output signals, memory means for storing the $N-M+1$ filtered signals, and correlation means responsive to the stored $N-M+1$ signals for producing a processed signal manifesting $N-M$ intercorrelation functions of said stored $N-M+1$ signals;
   adding means for forming a mean value output signal representing the mean value of the $N_F(N-M)$ intercorrelation functions of the processed signals of said channels; and
   interpolation means responsive to said mean value output signal for providing an estimate of the speed of the blood flow corresponding to said mean value output signal.

2. The device of claim 1 wherein said device has a sampling frequency of Fe, each said filter means being defined on the interval [O, Fe/2] by a modulus response equal to 1 and a random phase, and by a response zero for the frequency zero.

3. The device of claim 2 wherein each said memory means stores the sign of the $N-M+1$ signal supplied by the filter means of the corresponding channel.

4. The device of claim 3 further including validation means for validating the estimate provided by said interpolation means.

5. The device of claim 2 further including validation means for validating the estimate provided by said interpolation means.

6. The device of claim 1 wherein each said memory means stores the sign of the $N-M+1$ signal supplied by the filter means of the corresponding channel.

7. The device of claim 6 further including validation means for validating the estimate provided by said interpolation means.

8. The device of claim 1 further including validation means for validating the estimate provided by said interpolation means.

* * * * *